(12) United States Patent
Kassis et al.

(10) Patent No.: US 7,514,067 B2
(45) Date of Patent: Apr. 7, 2009

(54) METHODS FOR TUMOR DIAGNOSIS AND THERAPY

(75) Inventors: Amin I. Kassis, Chestnut Hill, MA (US); Ravi S. Harapanhalli, Silver Spring, MD (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/839,779

(22) Filed: Apr. 20, 2001

(65) Prior Publication Data

US 2003/0021791 A1 Jan. 30, 2003

Related U.S. Application Data

(60) Provisional application No. 60/199,350, filed on Apr. 25, 2000.

(51) Int. Cl.
*A61K 51/00* (2006.01)
*A61K 39/00* (2006.01)
*C12N 11/06* (2006.01)
*C12N 9/14* (2006.01)

(52) U.S. Cl. .................. 424/1.53; 424/178.1; 435/181; 435/195

(58) Field of Classification Search ............... 424/178.1, 424/1.53; 435/178.1, 181, 195
See application file for complete search history.

(56) References Cited

U.S. PATENT DOCUMENTS

| | | | | |
|---|---|---|---|---|
| 4,071,516 A | * | 1/1978 | Schwarz | 544/285 |
| 4,107,285 A | * | 8/1978 | Christenson | 436/542 |
| 4,975,278 A | * | 12/1990 | Senter et al. | 424/178.1 |
| 5,021,220 A | * | 6/1991 | Mertens | 424/1.85 |
| 5,316,906 A | * | 5/1994 | Haugland et al. | 435/4 |
| 5,489,525 A | * | 2/1996 | Pastan | 435/7.23 |
| 5,756,502 A | * | 5/1998 | Padia | 514/248 |
| 5,763,490 A | * | 6/1998 | Lebioda et al. | 514/574 |
| 5,816,259 A | | 10/1998 | Rose | 128/899 |
| 5,851,527 A | * | 12/1998 | Hansen | 424/178.1 |
| 5,854,968 A | * | 12/1998 | Horwitz et al. | 514/8 |
| 6,080,383 A | | 6/2000 | Rose | 424/1.69 |
| 6,156,739 A | * | 12/2000 | Griffin et al. | 514/80 |
| 6,265,427 B1 | * | 7/2001 | Camden | 514/388 |
| 6,361,774 B1 | * | 3/2002 | Griffiths et al. | 424/178.1 |
| 6,468,503 B2 | | 10/2002 | Rose | 424/1.69 |
| 6,495,553 B1 | * | 12/2002 | Shepard | 514/256 |
| 6,538,038 B1 | * | 3/2003 | Pero et al. | 514/731 |
| 2002/0147138 A1 | * | 10/2002 | Firestone et al. | 514/8 |

FOREIGN PATENT DOCUMENTS

EP 302473 A2 * 2/1989

OTHER PUBLICATIONS

Haugland "Handbook of Fluorescent Probes and Research Chemicals" 6th ediction, (Molecular Probes, Inc: Eugene, OR) 1996, pp. 220-224.*
Cox et al. "A high-resolution, fluorescence-based method for localization of endogenous alkaline phosphatase activity" J. Histochem. Cytochem. (1999) 47(11): 1443-1455.*
McCarty, M. "Non-toxic inhibition of extracellular tumor enzyme" Medical Hypotheses (1982) 8(3): 303-310.*
Unak et al. "Synthesis and Iodine-125 labeling of glucuronide compounds for combined chemo- and radiotherapy of cancer" Appl. Radiation Isotopes (1997) 48(6): 777-783.*
Unak, T. "Potential use of radiolabled glucuronide prodrugs with auger and/or alpha emitters in combined chemo- and radio-therapy of cancer" Current Pharmaceutical Design (2000) 6:1127-1142.*
Ho et al. "Radiolabeled prodrug (125I) ammonium 2-(2'-phosphorloxyphenyl)-6-iodo-4-(3H)-quinazolinone: Synthesis and biological evaluation" Abstracts of Papers, 221st ACS National Meeting, San Diego, CA, Apr. 1-5, 2001 MEDI-308.*

* cited by examiner

*Primary Examiner*—Irene Marx
*Assistant Examiner*—Susan Hanley
(74) *Attorney, Agent, or Firm*—Edwards Angell Palmer & Dodge LLP; George W. Neuner; Mark D. Russett

(57) ABSTRACT

The present invention discloses a method for the enzyme-mediated, site-specific, in-vivo precipitation of a water soluble molecule in an animal. The enzyme is either unique to tumor cells, or is produced within a specific site (e.g., tumor) at concentrations that are higher than that in normal tissues. Alternatively, the enzyme is conjugated to a targeting moiety such as an antibody or a receptor-binding molecule.

43 Claims, 8 Drawing Sheets

METHODS FOR TUMOR DIAGNOSIS AND THERAPY

CROSS-REFERENCES TO RELATED APPLICATIONS

This non-provisional U.S. national application, filed under 35 U.S.C. §111(a), claims the benefit of the filing date of a provisional U.S. national application Ser. No. 60/199,350 filed on Apr. 25, 2000 under 35 U.S.C. §111(b), the entirety of which is hereby incorporated by reference.

BACKGROUND OF THE INVENTION

Monoclonal antibodies (MAb), by virtue of their unique in-vitro specificity and high affinity for their antigen, have generally been considered particularly attractive as selective carriers of cancer radiodiagnostic/therapeutic agents. Several reasons underlie these expectations: (i) they show a high degree of specificity and affinity for their intended target; (ii) they are generally nontoxic; and (iii) they can transport such agents. The application of MAb in animals and humans for both tumor scintigraphic detection (labeled with $^{123}$I, $^{131}$I, $^{99m}$Tc, and $^{111}$In) and therapy (labeled with the beta emitters $^{131}$I, $^{186}$Re, $^{90}$Y, $^{165}$Dy, $^{67}$Cu, and $^{109}$Pd; the alpha emitters $^{211}$At, $^{212}$Bi, and $^{213}$Bi; or conjugated to various toxins and cytotoxic drugs) is the focus of work in many research laboratories.

In pursuing these studies, the basic assumption continues to be that MAb have a role in the radioimmunodiagnosis and radioimmunotherapy of cancer. However, while most published work on this subject has demonstrated their utility in the diagnosis and treatment of various tumors in experimental animal models, the use of radiolabeled MAb to target and treat solid tumors in cancer patients has been for the most part unsuccessful. There are at least five reasons for the results seen in humans:

1. Low tumor uptake. Thus far, most studies in humans have demonstrated that the percentage injected dose per gram of tumor (% ID/g) is extremely low. As a result, the absolute amount of the therapeutic radionuclide within the tumor is much less than that needed to deposit a radiation dose sufficiently high to sterilize the tumor.

2. High activity in the whole body. A corollary to low tumor uptake is the presence of ~90%-99% of the injected radiolabeled MAb in the rest of the body. This has led to the deposition of high doses in normal tissues and unacceptable side effects, and a reduction in the maximum tolerated dose (MTD).

3. Slow blood clearance. In most human radioimmunotherapy trials, whole MAb (MW ~150,000 Da) have been used. The clearance of such high-molecular-weight proteins from blood and nontargeted tissues is rather slow. The resulting systemic exposure to the radioisotope thus produces high doses to the bone marrow and a lowering of the MTD.

4. Limited intratumoral diffusion. The high molecular weight of MAb also limits their ability to extravasate and diffuse through the tumor mass. As a consequence, many areas within the tumor are spared from receiving a lethal dose of radiation (i.e., the areas are either outside the range of the emitted particle or receive a sublethal dose).

5. Heterogeneity of tumor-associated antigen expression. Many studies have demonstrated that a substantial proportion of the cells within a tumor mass show reduced/no expression of the targeted antigen. This also will lead to nonuniform distribution of the radionuclide within the tumor mass and the sparing of a large number of cells within the tumor.

In an attempt to bypass some of the limitations of these unique molecules, various two-step and three-step approaches have been theorized, in which a noninternalizing antitumor antibody is injected prior to the administration of a low-molecular-weight therapeutic molecule that has an affinity/reactivity with the preinjected antibody molecule. These systems can be categorized into two major classes: MAb-directed enzyme prodrug therapy and MAb-directed radioligand targeting, details of which are known in the art.

It is clear that under ideal conditions, a radiolabeled therapeutic agent must meet the following requirements: (i) be labeled with an energetic particle emitter, (ii) be taken up rapidly and efficiently by the tumor, (iii) be retained by the tumor (i.e. very long effective clearance half-life), (iv) have a short residence within normal tissues (i.e., short effective half-life in blood, bone marrow, and whole body), (v) achieve high tumor-to-normal tissue uptake ratios, (vi) attain an intratumoral distribution that is sufficiently uniform to match the range of the emitted particles (i.e. all tumor cells are within the range of the emitted particles), and (vii) achieve an intratumoral concentration that is sufficiently high to deposit a tumoricidal dose in every cell that is within the range of the emitted particle.

SUMMARY OF THE INVENTION

The present invention relates to a method for the enzyme-mediated, site-specific, in-vivo precipitation of a water soluble molecule in an animal. The enzyme is either unique to tumor cells (i.e. only produced by tumor cells), or is produced within the specific site (e.g., tumor) at concentrations that are higher than that in normal tissues. Alternatively, the enzyme is conjugated to a targeting moiety such as an antibody. For example, an antibody-enzyme conjugate is injected into tumor bearing animals and following tumor targeting and clearance from normal tissues and organs, the water soluble substrate is injected. Owing to the negatively charged prosthetic group (e.g. phosphate) present within its molecules, the substrate is highly hydrophilic, is not internalized by mammalian cells, and should clear from circulation at a rate that is compatible with its physical characteristics (e.g. molecular weight, charge). However, being a substrate for the enzyme (pre-targeted or otherwise), this water soluble molecule loses the prosthetic group and the resulting molecule precipitates out due to its highly water-insoluble nature. The precipitated molecule is thus "indefinitely trapped" within the targeted tissue. In one of its aspects (Enzymatic Radiolabel Insolubilization Therapy, ERIT), the substrate is radiolabeled with a gamma or a positron emitting radionuclide and as such, the location of the precipitate can be detected by external imaging means (SPECT/PET). On the other hand, when the radionuclide is an alpha or a beta particle emitter, the trapped precipitated radioactive molecule will maintain the radionuclide within the targeted tumor thereby enhancing its residence time and delivering a high radiation dose specifically to the tumor relative to the rest of the body. In yet another aspect (Enzymatic Boron Insolubilization Therapy, EBIT), the substrate is conjugated to one/more boron-containing molecule and upon precipitation within its intended target, the tumor is subjected to epithermal neutrons with the subsequent alpha particle emissions (Boron Capture Therapy).

In its simplest form, therefore, the present invention is based on the conversion of a chemical (e.g. quinazolinones, benzoxazoles, benzimidazoles, benzothiazoles, indoles, and derivatives thereof) from a freely water-soluble form to a highly water-insoluble form and hence in vivo precipitation at the specific site where an enzyme (e.g., one of acetyiglucosaminidases, acetylneuraminidases, aldolases, amidotranferases, arabinopayranosidases, carboxykinases, cellulases, deaminases, decarboxylases, dehydratases, dehydrogenases, DNAses, endonucleases, epimerases, esterases, exonucleases, fucosidases, galactosidases, glucokinases, glucosidases, glutaminases, glutathionases, guanidinobenzodases, glucoronidases, hexokinases, iduronidases, kinases, lactases, mannosidases, nitrophenylphosphatases, peptidases, peroxidases, phosphatases, phosphotransferases, proteases, reductases, RNAses, sulfatases, telomerases, transaminases, transcarbamylases, transferases, xylosidases, uricases, or urokinases) or any other species capable of carrying out such a conversion in high concentrations. Pretargeting of enzyme or its equivalent species may be achieved by making use of specific antibodies or any such specific receptor-binding ligand to the desired sites in vivo. Note that the ligand may also be a peptide or hormone, with the receptor specific to the peptide or hormone. Alternatively, the enzyme may be produced within the tumor site by the tumor cells themselves or following gene therapy or similar means. The chemical to be injected in the second step contains any nuclide suitable for imaging and/or therapy (e.g. Boron-10, Carbon-11, Nitrogen 13, Oxygen-15, Fluorine-18, Phosphorous-32, Phosphorous-33, Technetium-99m, Indium-111, Yttrium-90, Iodine-123, Iodine-124, Iodine-131, Astatine-211, Bismuth-212, etc.).

BRIEF DESCRIPTION OF THE DRAWINGS

The accompanying drawings illustrate preferred embodiments of the invention as well as other information pertinent to the disclosure, in which.

DESCRIPTION OF THE PREFERRED EMBODIMENTS

Figure 1:
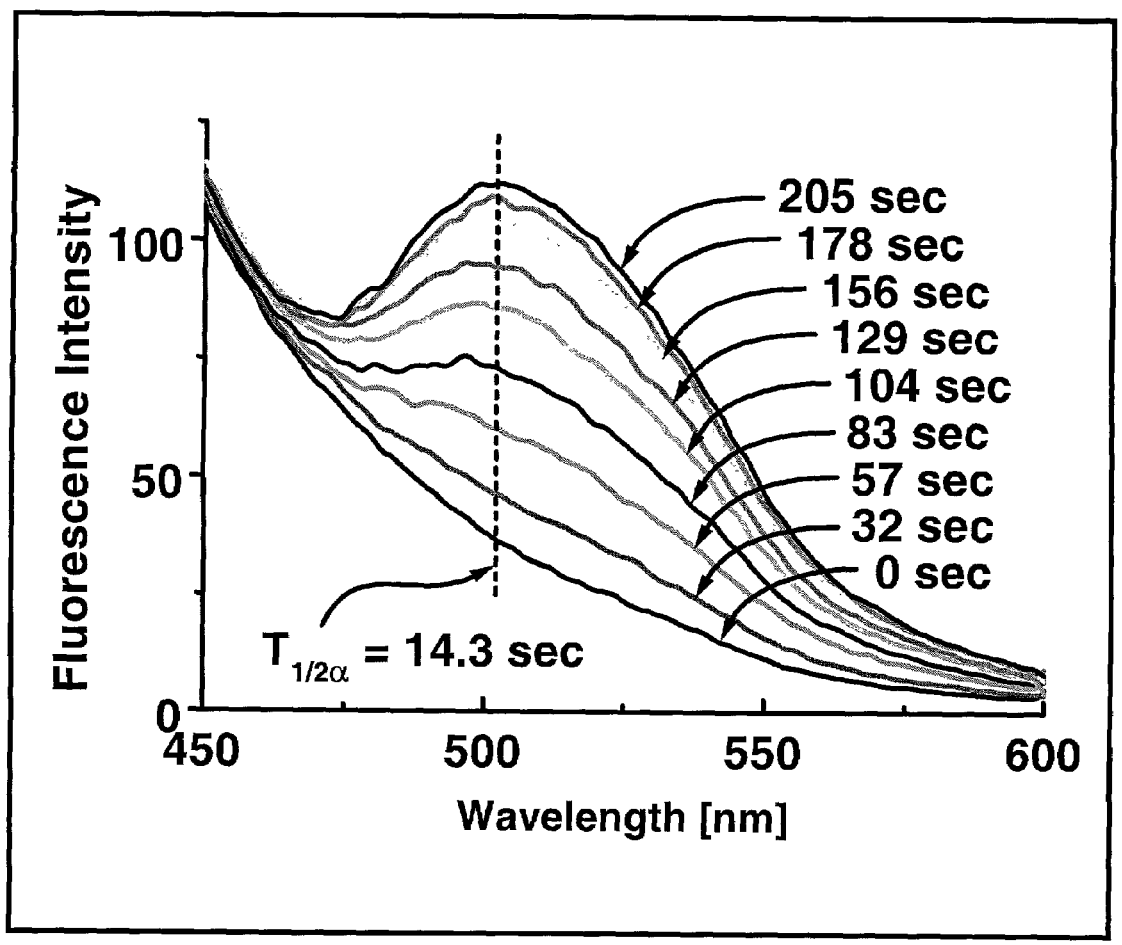
FIG. 1 is a graph of a time-course conversion of 1 (or Compound A) to 2 (or Compound B) following incubation in alkaline phosphatase.

This invention describes a novel approach that serves to localize water-insoluble, radioactive molecules within the extracellular (interstitial) space of a tumor. In one embodiment of this invention, a noninternalizing monoclonal antibody (MAb) to a "tumor-specific" antigen is chemically conjugated to the enzyme alkaline phosphatase (ALP); the MAb-ALP conjugate is administered intravenously (i.v.) to tumor-bearing animals, and after MAb-ALP tumor localization and clearance from circulation (high tumor to normal tissue ratios), a water-soluble, radiolabeled prodrug (PD) that is a substrate for ALP is injected intravenously. The conjugate or prodrug may also be injected intra-arterially, subcutaneously, into the lymphatic circulation, intraperitoneally, intrathecally, intratumorally, intravesically, or is given orally.

The prodrug substrate is represented by the following formula:

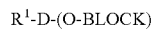

$R^1$-D-(O-BLOCK)

wherein BLOCK is a blocking group that can be cleaved from the remainder of the substrate by action of an enzyme, resulting in a water-insoluble drug molecule represented by the following formula:

$R^1$-D-O-H wherein D contains a minimum of 2 linked aromatic rings, and $R^1$ is a radioactive atom, a molecule labeled with one or more radioactive atom(s), a boron atom, or a molecule labeled with one or more boron atoms.

The radiolabel is selected from the group consisting of a gamma emitting radionuclide suitable for gamma camera imaging, a positron emitting radionuclide suitable for positron emission tomography, and an alpha or a beta particle emitting radionuclide suitable for therapy. The alpha particle emitting radionuclide may be, e.g., astatine-211, bismuth-212, or bismuth-213. The beta particle emitting radionuclide emits beta particles whose energies are greater than about 1 keV. The beta particle emitting radionuclide may be, e.g., iodine-131, copper-67, samarium-153, gold-198, palladium-109, rhenium-186, rhenium-188, dysprosium-165, strontium-89, phosphorous-32, phosphorous-33, or yttrium-90. Note also that the boron atom is suitable for neutron activation.

The BLOCK is selected from the group consisting of:

a monovalent blocking group derivable by removal of one hydroxyl from a phosphoric acid group, a sulfuric acid group, or a biologically compatible salt thereof;

a monovalent blocking group derivable by removal of a hydroxyl from an alcohol or an aliphatic carboxyl, an aromatic carboxyl, an amino acid carboxyl, or a peptide carboxyl; and a monovalent moiety derived by the removal of the anomeric hydroxyl group from a mono- or polysaccharide.

As the PD molecules percolate through the tumor mass, they will be hydrolyzed by the ALP molecules present within the tumor (MAb-ALP). The hydrolysis of PD (Compound 1, or Compound A below) leads to the formation of a water-insoluble, radiolabeled precipitate (D). It is anticipated that D (Compound 2, or Compound B below), as a consequence of its physical properties, will be trapped within the extracellular space of the tumor mass. Thus, when labeled with iodine-131 ($^{131}$I), a radionuclide that decays by the emission of both a beta particle ($E_{max}$=610 keV; mean range=467 μm; maximum range=2.4 mm) and photons suitable for external imaging, the entrapped $^{131}$I-labeled D molecules will serve as a means for both assessing tumor-associated radioactivity (planar/SPECT) and delivering a protracted and effective therapeutic dose to the tumor.

Enzymatic hydrolysis of radiolabeled quinzalinone prodrugs

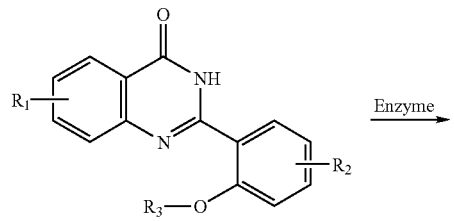

Water-soluble radioactive substrate (1)

$R_1 = {}^{123}I, {}^{125}I, {}^{131}I, {}^{77}Br, {}^{211}At$ etc and $R_2 = H$
$R_1 = H$ and $R_2 = {}^{123}I, {}^{125}I, {}^{131}I, {}^{77}Br, {}^{211}At$ etc
$R_1, R_2$ = Boron cage and/or H
$R_3$ = phosphate, sulphate, galactosyl, etc.

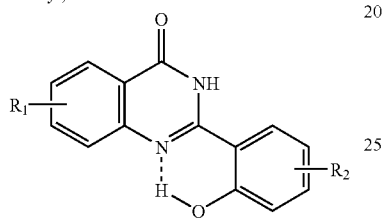

Radioactive precipitate
(or Organoboron precipitate)

(2)

Radiolabeled 2-(2'-hydroxyphenyl)-4-(3H)-quinazolinone dyes are employed in the method of the present invention: These classes of compounds contain a hydroxyl group that forms an intramolecular six-membered stable hydrogen bond with the ring nitrogen and hence they are highly water-insoluble in nature. However, addition of a prosthetic group (e.g. phosphate, sulfate, sugars such as galactose or peptide) on the hydroxy group renders the molecule freely water-soluble. Furthermore, the presence of such prosthetic groups makes cell membranes impermeable to these molecules; they are anticipated to have relatively short biological half-lives in the blood. However, when acted on by the enzyme, the prosthetic group is lost, resulting in the restoration of intramolecular hydrogen bonding, and the molecule becomes water-insoluble and precipitates.

The procedure for the synthesis of the unsubstituted quinazolinone dye (1, below), is as follows:

Synthesis of
2-(2'hydroxyphenyl)-4-(3H)-quinazolone

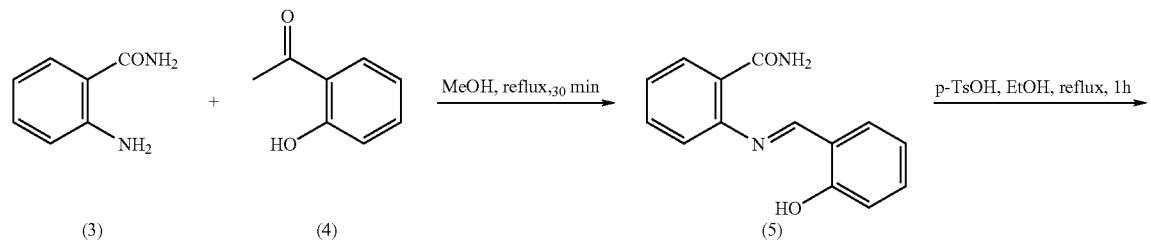

(3)        (4)                                    (5)

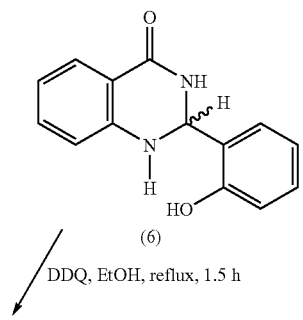

(6)

DDQ, EtOH, reflux, 1.5 h

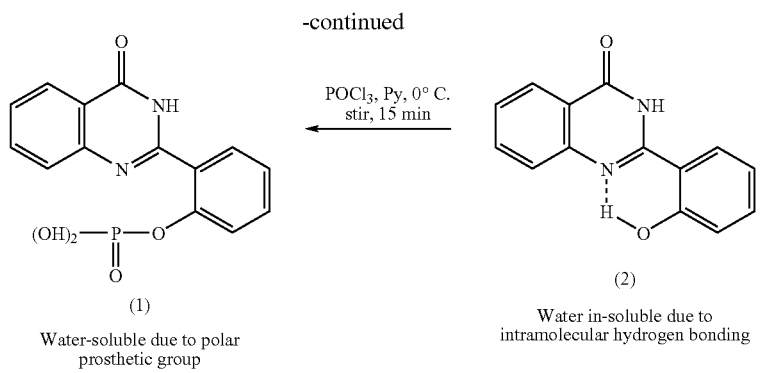

(1) Water-soluble due to polar prosthetic group (2) Water in-soluble due to intramolecular hydrogen bonding 1.3 g anthranilamide (3) and 1.2 g salicylaldehyde (4) were refluxed in methanol. Within 30 minutes, a thick orange precipitate of the Schiff-base (5) was formed. The reaction mixture was cooled in a refrigerator and the product filtered and washed with cold methanol. The precipitate (about 1.5 g) was then suspended in 20 ml ethanol containing p-toluene sulfonic acid and refluxed for 1 hour. The progress of reaction was followed by TLC. The off-white precipitate of dihydroquinazolinone (6) was filtered off and washed thoroughly with cold ethanol. It was then suspended in 12 ml methanol containing 0.6 g dichloro-dicyanobenzoquinone and heated under reflux for 1 hour. The quinazolinone dye product (2) was isolated after cooling the reaction mixture and subsequent filtration. The pale yellow chemical was suspended in diethyl ether and stirred, filtered and washed with ether. To 100 mg of the quinazolinone dye (2) in 1 ml of dry pyridine under nitrogen in an ice bath was added 65 mg (40 µl) of POCl$_3$ through a syringe. After stirring at this temperature for 30 minutes, it was neutralized by the addition of 116 µl of 30% ammonia. The crude product (1) was evaporated to dryness in rotary evaporator and was partitioned between ethyl acetate and water, the organic layer re-extracted with water, and the combined aqueous extract was back extracted with ethyl acetate. Finally, the product was loaded on to a DEAE Sephacel column (10 ml) pre-equilibrated in bicarbonate form. The column was washed with 20 ml water followed by a stepwise gradient of triethyl ammonium bicarbonate buffer (pH 7.0, 0.1 M to 0.5 M, 25 ml each). Appropriate fluorescent fractions were pooled and lyophilized to dryness (yield 55%). All chemicals were characterized by NMR and elemental analysis.

In order to make use of the above chemistry for the synthesis of radiolabeled quinazolinones, halogen substituted anthranilamides that are easily converted to the tin prescursors needed for the exchange labeling with radiohalogens were used. Thus, for the synthesis of 5-haloanthranilamides (9) from 5-haloanthranillic acids (7), isatoic anhydrides were used, as shown below.

Synthesis of 5-halo-anthranilamides from 5-halo-anthranilic acids

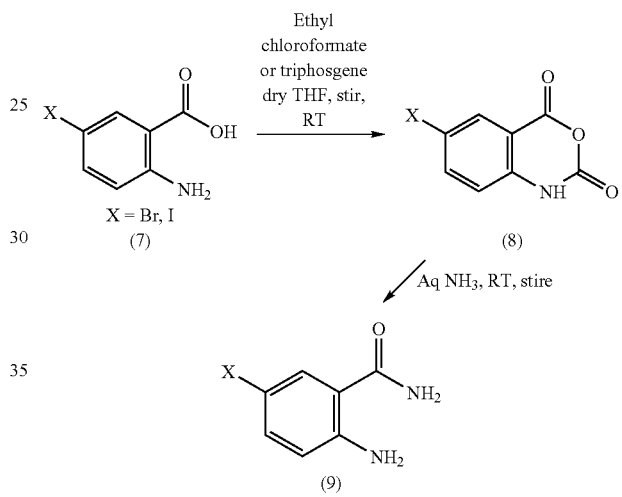

Such anhydrides are known to react with amines to furnish anthranilamides under certain controlled conditions. Since phosgene gas is not available, reaction conditions were employed using triphosgene which is a solid. 5-Halo-anthranilic acid (bromo- or iodo-) was stirred with equimolar amounts of triphosgene in dry THF at ambient temperature for 1-2 hours. The solution was filtered and diluted with hexane until it became turbid and then stored at −20° C. overnight. The precipitated anhydride (8) was filtered and washed copiously with hexane THF mixture and dried (yield ~60%). The anhydride (dissolved in THF) was stirred in 1 M aqueous solution of ammonia (containing 1:1 THF) at ambient temperature for 25 minutes. Finally, the organic layer was evaporated under nitrogen and the product (9) was filtered and washed copiously with water followed by acetonitrile and dried in vacuo (yield ~75%).

2-Amino-5-iodobenzoic acid (10) and triphosgene were then dissolved in dry THF and the reaction mixture stirred at room temperature for 1 hour. An off-white precipitate formed and TLC showed that compound 10 is consumed, as shown below. The precipitate was filtered, washed with cold methanol, and crystallized in acetonitrile. $^1$H NMR indicated that the spectrum was an iodoisotoic anhydride (11).

Synthesis of non-radioactive ($^{127}$I) prodrug (15)

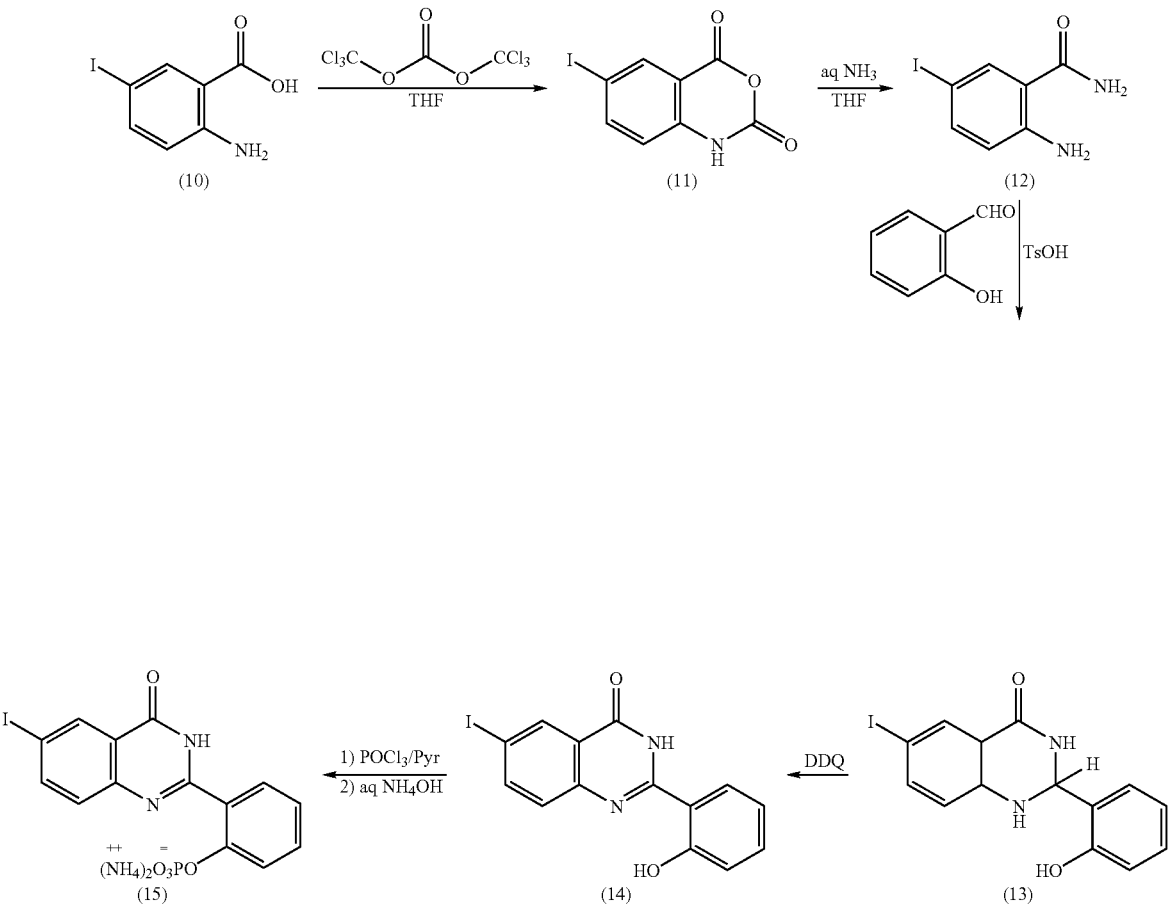

A solution of iodoisotoic anhydride (11) was then suspended in THF and cooled in an ice-bath. Aqueous ammonium hydroxide was added dropwise, the reaction mixture was stirred for 15 minutes at 0°C. and 30 minutes at RT, and the solvent was evaporated. The white solid obtained was characterized by $^1$H NMR and identified as an iodoanthranilamide (12).

Next, Iodoanthranilamide (12) and salicylaldehyde were suspended in methanol and refluxed in the presence of catalytic amounts of p-toluene sulfonic acid (TsOH) for 30 minutes. To the pale-yellow precipitate (13) formed, 2,3-dichloro-5,6-dicyano-1,4-benzoquinone was added and the suspension was refluxed for 1 hour. The solid product was filtered, washed with cold methanol, characterized by $^1$H NMR, and identified as 2-(2'-Hydroxyphenyl)-6-iodo-4-(3H)-quinazolinone.

Synthesis of Ammonium 2-(2'-Phosphoryloxyphenyl)-6-iodo-4-(3h)-quinazolinone (15).

In one method, 2-(2'-Hydroxy)-6-iodo-4-(3H-quinazolinone (14) was added to dried pyridine at 0°C., followed by phosphorus oxychloride. Silica gel TLC indicated that the reaction was completed within 2 min. The reaction solution was neutralized to pH 7.0 by the addition of ammonium hydroxide. The solvent was evaporated and the solid product was suspended in water, filtered, and purified by chromatography. Following elution (stepwise gradient: water followed by acetonitrile-water, 2:1), a yellow solution containing UV-visible product was collected, the solvent was evaporated, and the product was characterized by $^1$H and $^{31}$P NMR and identified as compound 15.

In an alternative method, ammonium 2-(2'-phosphoryloxyphenyl)-6-tributylstannyl-4-(3H)-quinazolinone (17) was dissolved in methanol, and sodium iodide was added followed by hydrogen peroxide. A yellow precipitate formed immediately. The reaction vial was vortex-mixed and incubated for 30 minutes at 37° C. Reversed-phase silica gel TLC showed approximately 50% conversion (solvent: acetonitrile-water, 1:1). The solvent was evaporated and the product purified by chromatography. TLC (solvent: chloroform-methanol, 1:1) showed the same $R_f$ value (0.6), and proton and $^{31}$P NMR gave the same spectra as were obtained with the known compound 15 synthesized by the route shown above.

Synthesis of compounds 18 and 15 by iododestannylation

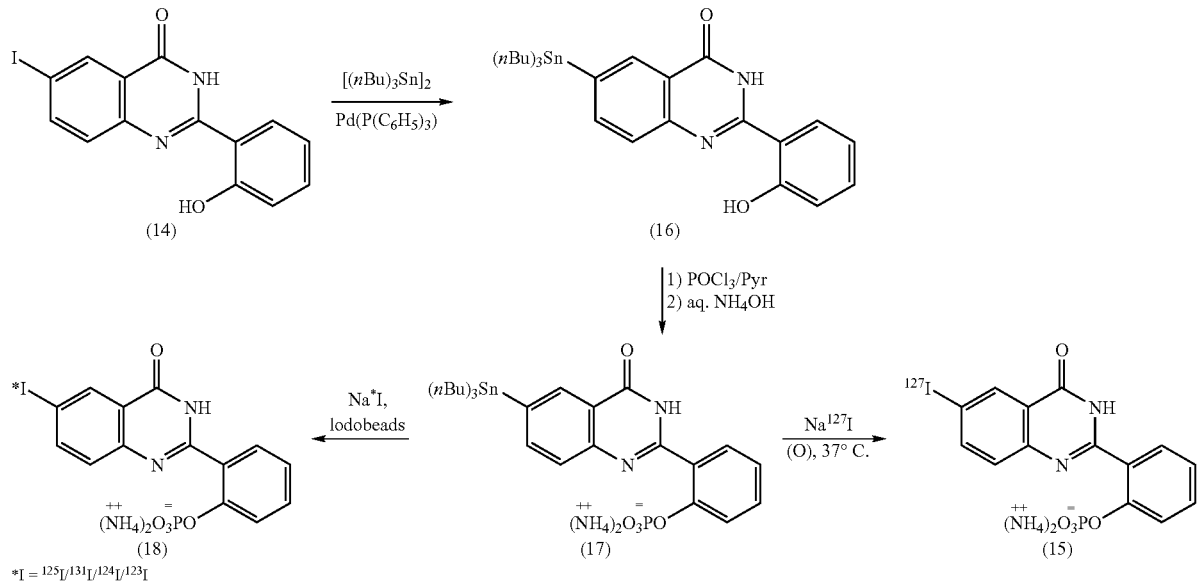

Next, to a dioxane solution containing 14, hexa-n-butylditin and tetrakis(triphenylphosphine)palladium were added, as shown above. The reaction mixture was refluxed for 1.5 hours and progress of the reaction was followed by silica gel TLC (solvent: methylene chloride-ethyl acetate, 9:1) to test for the formation of a more nonpolar product. The solvent was evaporated, and the crude yellow solid was purified on a silica gel column (stepwise gradient: starting with hexane followed by hexane-dichloromethane, 1:1). Following solvent evaporation, a yellow fluorescent solid 2-(2'-Hydroxy)-6-tributylstannyl-4-(3H)-quinazolinone 16 was obtained as identified by $^1$H NMR.

Next, to a stirred solution of 16 in dry pyridine cooled to 0°C., phosphorus oxychloride was added dropwise. The reaction mixture was stirred for 10 min at 0°C. and then quenched by the addition of ammonium hydroxide (Scheme 5). The solvent was evaporated, the crude product redissolved in methanol-acetate (1:1) and purified on a $C_{18}$ column (stepwise gradient: water followed by acetonitrile-water going from 30% to 50% acetonitrile). The solvent was evaporated and the nonfluorescent solid Ammonium 2-(2'-Phosphoryloxyphenyl)-6-tributylstannyl-4-(3H)-quinazolinone 17 was obtained as identified by $^{31}$P NMR.

Next, three Iodo-beads were placed in a reaction vial, followed by 20 µl of 1 µg/µl solution of 17, 30 µl 0.1 M borate buffer (pH=8.3), and Na$^{125}$I (800 µCi/8 µl of 0.1 M sodium hydroxide). After 20 minutes at room temperature, the crude reaction mixture was loaded on a Sep-Pak Plus $C_{18}$ cartridge and eluted with 1 ml water and then 2 ml 10% acetonitrile in water. The product 18 was eluted with 20% acetonitrile in water (yield: ~370 µCi; radiochemical yield: 46%). The radiolabeled product, co-spotted with nonradioactive compound 15 on reversed-phase TLC, showed a single spot on autoradiograph (solvent: acetonitrile-water, 1.5:2). Radiolabeled ($^{125}$I) Ammonium 2-(2'-Phosphoryloxyphenyl)-6-iodo-4-(3H)-quinazolinone 18 co-injected with 15 into the HPLC showed a single radioactive peak ($R_f$=14 min) which matched the $R_f$ value of 15.

X-Gal (5-bromo-4-chloro-3-indolyl β-D-galactose) is routinely used for the identification of lac$^+$ bacterial colonies. The underlying principle is that the colorless X-gal which is freely water-soluble is converted to dark blue colored precipitate upon reaction with b-galactosidase enzyme.

Enzymatic hydrolysis of X-gal type prodrugs

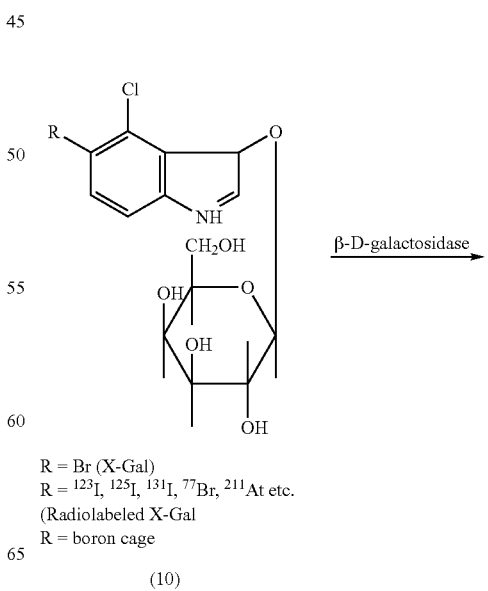

R = Br (X-Gal)
R = $^{123}$I, $^{125}$I, $^{131}$I, $^{77}$Br, $^{211}$At etc.
(Radiolabeled X-Gal)
R = boron cage (10)

-continued

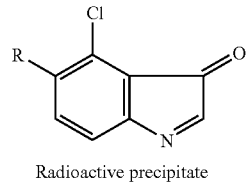

Radioactive precipitate
(or Organoboron precipitate)

(11)

In accordance with the present invention, a bromine atom within X-gal is replaced with a diagnostic/therapeutic nuclide (e.g. Iodine-131, boron-10). For example, an antibody-β-galactosidase immunoconjugate will be administered in the first step. Following its clearance, the water soluble nuclide-labeled X-gal (10) will be injected where at the sites of enzyme action, the X-gal substrate will loose the sugar moiety and the resulting aglycon (11) will precipitate within the targeted tissue. In another embodiment, prosthetic groups other than galactosyl (e.g. phosphate, sulfate, carbonate) as well as nuclides other than iodine-131 and boron-10 may be used.

When the prodrug ((1) or Compound A), a non-fluorescent, stable, water-soluble compound, is incubated (37° C.) with alkaline phosphatase (ALP), a bright yellow-green fluorescent, clearly visible precipitate is formed whose $R_f$ on thin layer chromatography (TLC) corresponds to drug ((2) or Compound B). In order to assess the kinetics of this enzyme-based hydrolysis (i.e. conversion of Compound A to Compound B) at 37° C., Compound A (60 µM) was mixed with 10 units ALP in 0.1 M Tris (pH 7.2) and the reaction kinetics followed over time using a Perkin-Elmer LS50B Luminescence Spectrometer with excitation at 340 nm and emission at 500 nm. There is a rapid increase in fluorescence intensity under these experimental conditions, as shown in FIG. 1, demonstrating the hydrolysis of Compound A and the formation of Compound B. No fluorescence was observed when the enzyme was heat-inactivated prior to its incubation with Compound A.

Figure 2:
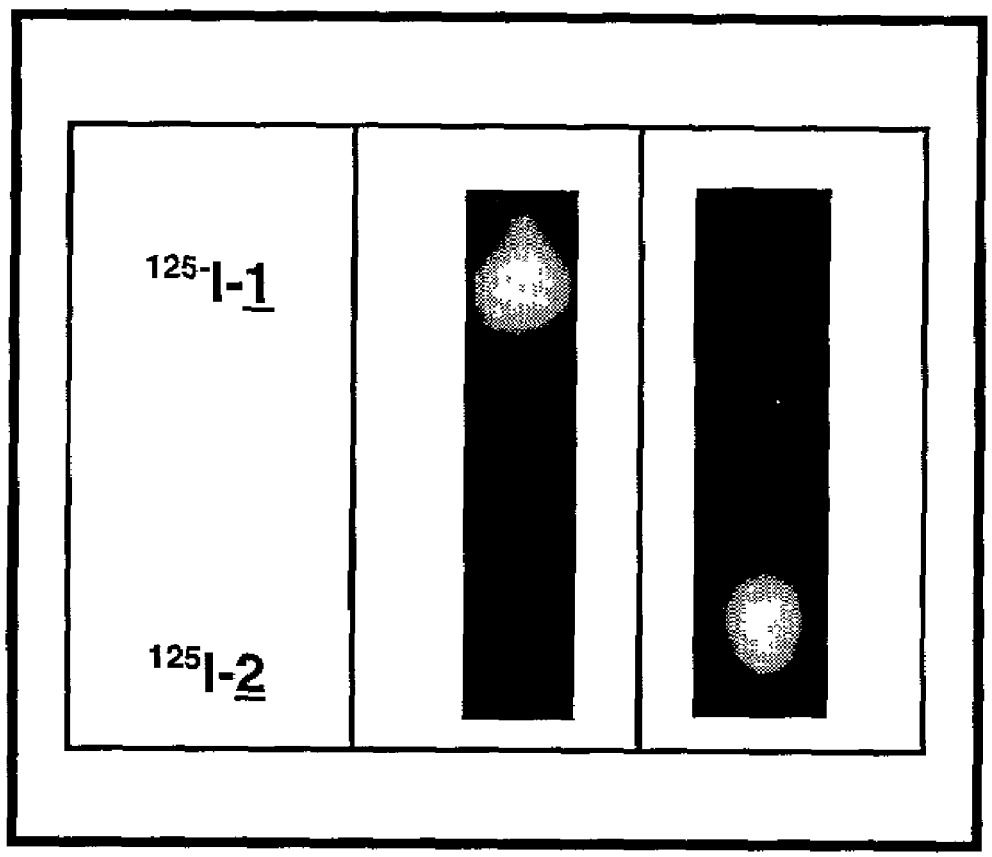
FIG. 2 is an illustration of the conversion of $^{125}$I-1 ($^{125}$I-labeled Compound A) to $^{125}$I-2 ($^{125}$I-labeled Compound B) following incubation with ALP.

In order to further characterize the $^{125}$I-labeled prodrug, $^{125}$I-labeled Compound A (~10 µCi/100 µl 0.1 M Tris buffer, pH 7.2) was incubated with 5 units ALP or heat-inactivated (70° C., 2 hours) ALP; the samples were spotted on reversed-phase TLC plates that were then run in acetonitrile-water (1.5:2). Autoradiography demonstrates the complete conversion of $^{125}$I-labeled Compound A to $^{125}$I-labeled Compound B only in the presence of the active enzyme, as shown in FIG. 2.

Figure 3:
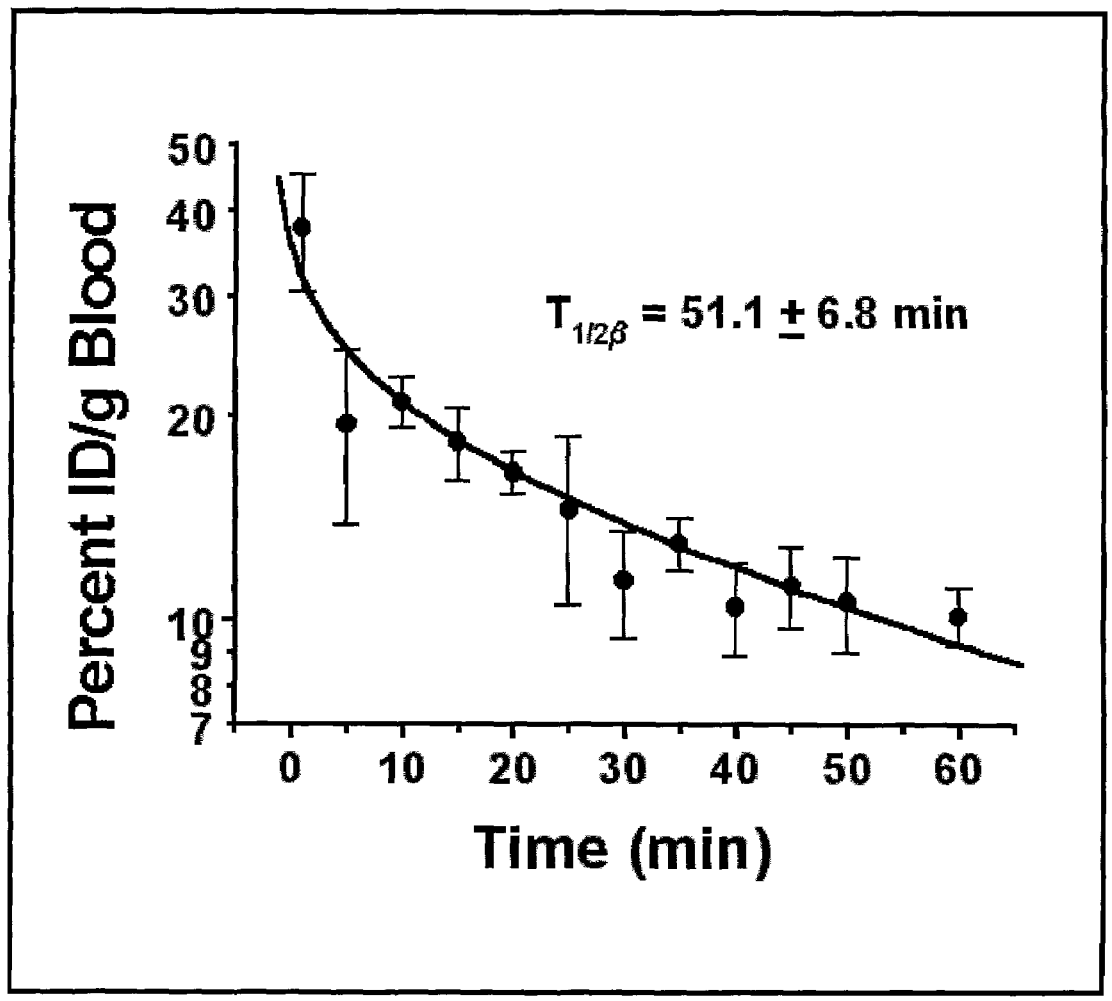
FIG. 3 is a graph of radioactivity following i.v. injection of $^{125}$I-1 into mice.

In order to determine blood clearance of AP$^{125}$IQ, mice (n=5/group) were injected i.v. with the radioiodinated prodrug and bled over a 1 hour period, the radioactive content per gram of blood was measured, and the percentage injected dose per gram (% ID/g) calculated. The results as shown in FIG. 3 demonstrate a rapid biphasic blood clearance of radioactivity and a $T_{1/2\beta}$ of 51.1±6.8 min.

In order to assess the chemical nature of the radioactivity in blood (i.e. determine stability of $^{125}$I-labeled Compound A in blood), ethanol was added to the blood samples (collected during the first 40 min), the tubes were centrifuged, and the supernatant was spotted on TLC. The plates were run in acetonitrile-water (1.5:2) and autoradiographed. The results show (i) the presence of a single spot whose $R_f$ is the same as that observed with $^{127}$I-labeled Compound A, and (ii) no evidence of free iodine. These data demonstrate the stability of I-labeled Compound A in serum.

Figure 4:
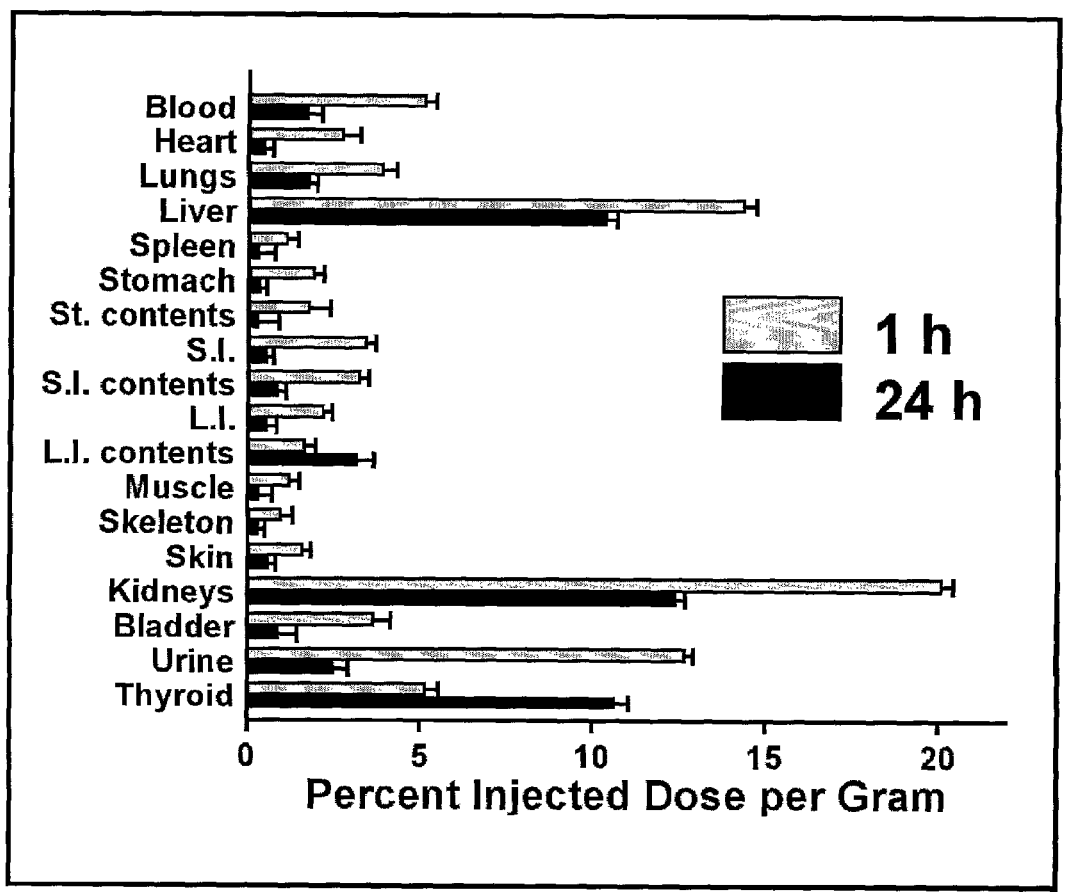
FIG. 4 is an illustration of the biodistribution of $^{125}$I-1 in normal mice.

The biodistribution of $^{125}$I-labeled Compound A in normal tissues was also considered. Mice (n=30) were injected i.v. with the radiopharmaceutical (~5 µCi/100 µl), the animals were killed at 1 hour (n=15) and 24 hours (n=15), and the radioactivity associated with blood, tissues, and organs was determined. As shown in FIG. 4, (i) the radioactivity in all organs and tissues declined over time; (ii) the radioactivity in the kidneys and urine was high, suggesting that the compound and/or its metabolic breakdown/hydrolysis products were rapidly excreted (since the weight of the thyroid is ~5 mg, the activity within the thyroid indicates minimal dehalogenation of the compound); and (iii) <20% of the injected dose remained in the body by 24 hours. These results, therefore, demonstrate that $^{125}$I-labeled Compound A and/or its metabolic breakdown/hydrolysis product(s) have a low affinity to normal tissues and that the presence of endogenous ALP leads to minimal hydrolysis of the compound.

Figure 5:
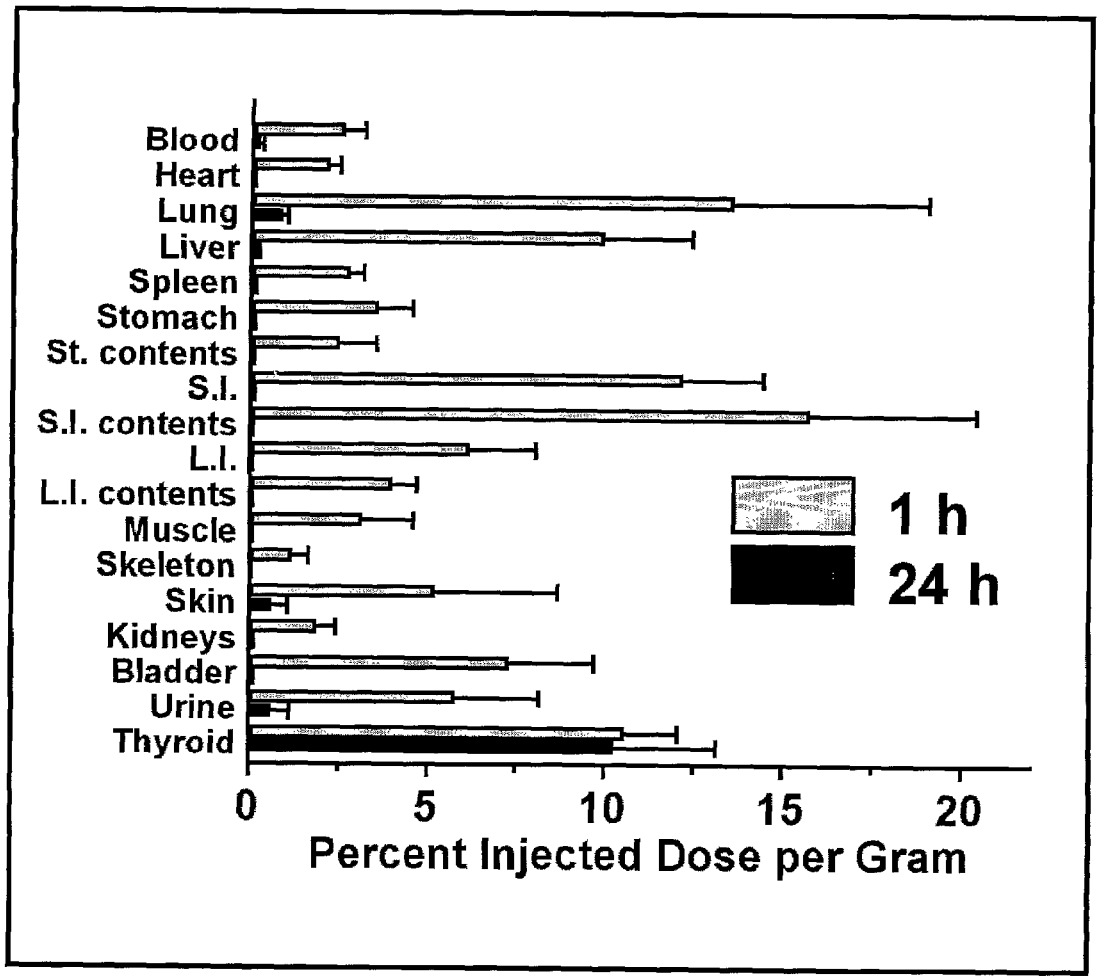
FIG. 5 is an illustration of the biodistribution of $^{125}$I-2 in normal mice.

The biodistribution of $^{125}$I-labeled Compound B was also examined in various tissues in normal mice. In these experiments, $^{125}$I-labeled Compound A was synthesized, purified, and incubated at 37° C. in the presence of ALP overnight. TLC demonstrated the complete conversion of $^{125}$I-labeled Compound A to $^{125}$I-labeled Compound B. Mice (n=10) were injected i.v. with $^{125}$I-labeled Compound B (~5 µCi/100 µl) and killed (n=5) at 1 hour and 24 hours. The 1 hour data, as shown in FIG. 5, demonstrate the presence of this water-insoluble molecule in all the tissues examined (<15% ID/g). However, by 24 hours (FIG. 5), all tissues and organs (with the exception of minimal activity in the thyroid) were virtually void of radioactivity (<4% of the injected dose remained in the body by 24 hours). These results show that $^{125}$I-labeled Compound B has no avidity for any tissue in the mouse and that the tissue-associated activity seen at 1 hour reflects that within the blood. Since these data seem to argue for the inability of $^{125}$I-labeled Compound B to traverse blood vessel walls and enter into tissues, this water-insoluble molecule if formed within a tissue (e.g. tumor mass) is likely to be retained, i.e. it will not leach back into circulation.

Figure 6:
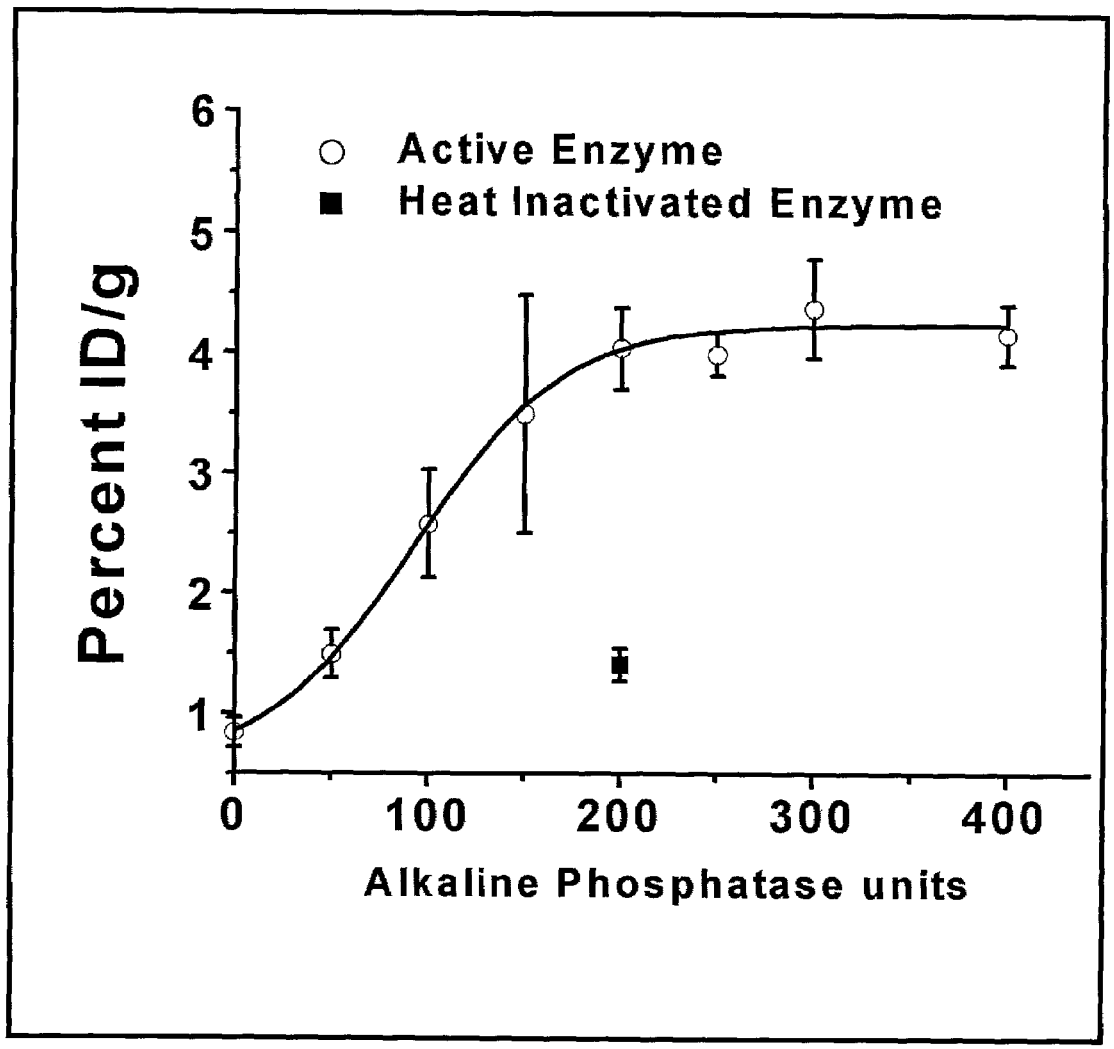
FIG. 6 is a graph of the accumulation of radioactivity within forelimbs of mice after subcutaneous (s.c.) injection of alkaline phosphatase followed by i.v. injection of $^{125}$I-2.

In order to demonstrate within an animal the conversion of the water-soluble $^{125}$I-labeled Compound A to the water-insoluble $^{125}$I-labeled Compound B, ALP was dissolved in saline (50, 100, 150, 200, 250, 300, 400 units/10 µl) and using a 10-µl syringe, 10 µl enzyme preparation was injected s.c. in the forelimb of Swiss Alpine mice. Five-minutes later, 20 µCi $^{125}$I-labeled Compound A was injected i.v. (tail vein). The animals were killed 1 hour later and the radioactivity in the forelimbs was measured. The results, as shown in FIG. 6, demonstrate that the radioactive content within the forelimbs of animals pre-injected with ALP increased with enzyme dose and plateaued at the highest concentrations. The fact that these increases were due to the enzymatic action of ALP was ascertained in studies that showed no increase in uptake in the forelimbs of mice pre-injected with heat-inactivated ALP (FIG. 6). These results illustrate the specific dose-dependent accumulation of $^{125}$I-labeled Compound A (more accurately, $^{125}$I-labeled Compound B) within alkaline-phosphatase-containing sites in an animal.

Figure 7:
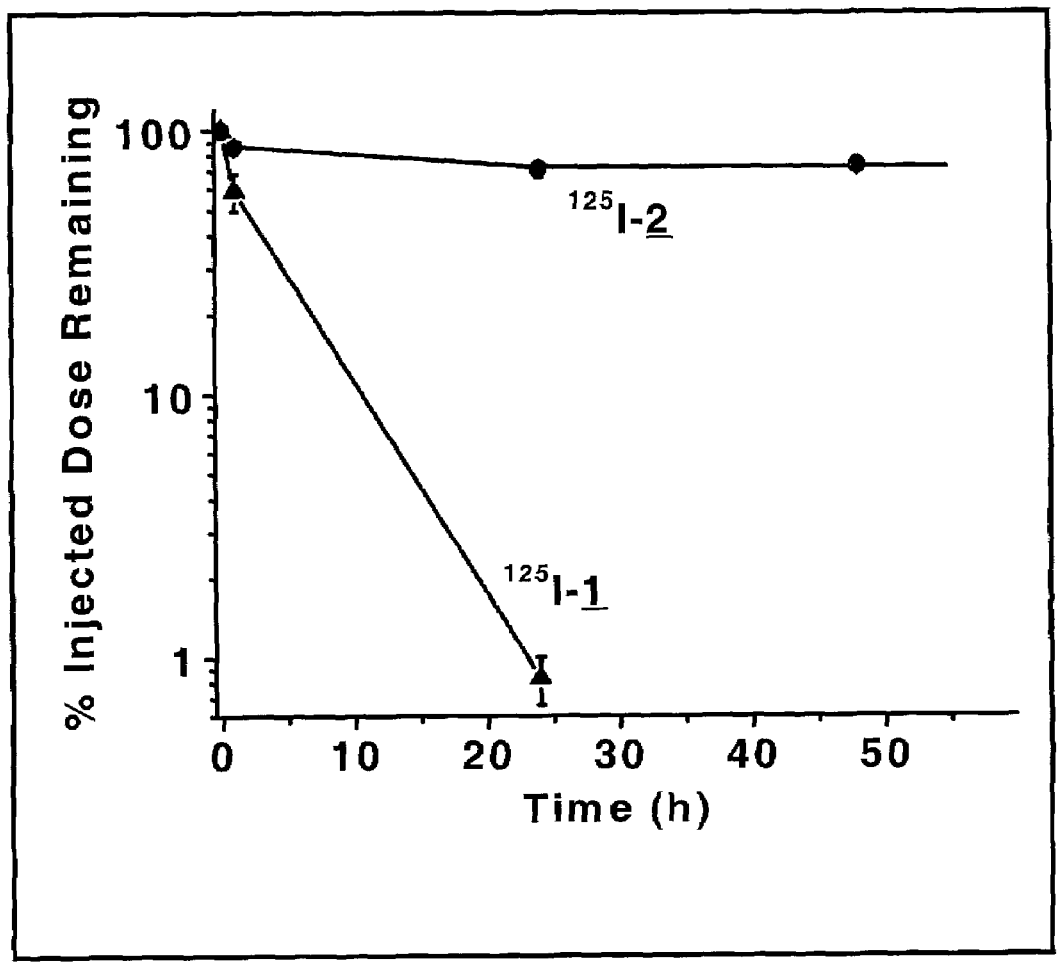
FIG. 7 is a graph depicting the retention of radioactivity within a forelimb of mice injected s.c. with $^{125}$I-1 or $^{125}$I-2.
Figure 8:
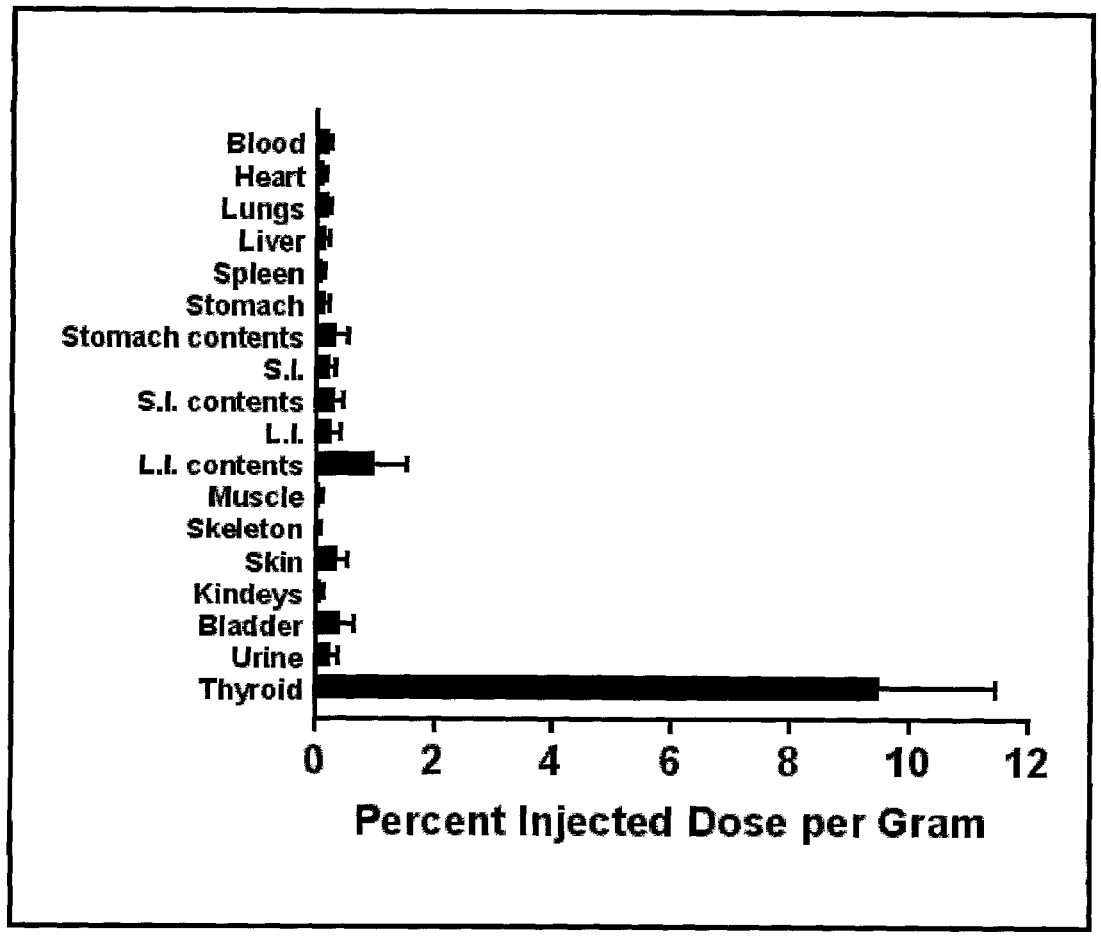
FIG. 8 is an illustration of the biodistribution (24 hours) of s.c.-injected $^{125}$I-2 in normal mice.

In order to demonstrate that once formed, the water-insoluble Compound B is retained "indefinitely" within the tissue where it is formed, $^{125}$I-labeled Compound B was dissolved in 100 µl DMSO (under these conditions, $^{125}$I-labeled Compound B is completely soluble in DMSO; however, when 100 µl water are added, a visible precipitate forms immediately that contains $^{125}$I-labeled Compound B radioactivity). Five µl of this solution was injected s.c. into the right forelimb of mice (n=15), followed by 5 μl saline. For comparison, $^{125}$I-labeled Compound A (5 μCi/5 μl saline) was injected s.c. into the left forelimb of the same mice and followed with 5 μl DMSO. The animals were killed after 1 hour, 24 hours, and 48 hours, the radioactivity associated with the forelimbs was measured, and the percentage of radioactivity remaining was calculated (at the 24 hour time point, the biodistribution of radioactivity in various tissues and organs was also determined). The data (FIG. 7) demonstrate that while greater than about 98% of the prodrug $^{125}$I-labeled Compound A had seeped out of the s.c. pocket by 24 hours, 71±5% of the injected precipitable $^{125}$I-labeled Compound B activity remained at the injection site at 24 hours. The biodistribution data (FIG. 8) show that the radioactivity that escaped during the first 24 hours following the s.c. injection of $^{125}$I-labeled Compound B does not localize in any normal tissues within the animal (activity within the thyroid indicates uptake of free iodine). Finally, the results show no change in the radioactivity in the forelimbs of the animals at 24 hours and 48 hours (FIG. 7), thereby indicating that the precipitated $^{125}$I-labeled Compound B is permanently and indefinitely trapped within tissues.

While this invention has been described in terms of exemplary embodiments, it is not limited thereto. Rather, the appended claims should be construed broadly to include other variants and embodiments of the invention which may be made by those skilled in the art without departing from the scope and range of equivalents of the invention.

We claim:

1. A method of in-vivo localizing a water-insoluble drug within the extracellular space of solid tumor tissue in an animal, the method comprising administering a water-soluble prodrug to the animal, wherein the prodrug comprises the drug substituted with a prosthetic group that is cleavable by an enzyme, which is present in the extracellular space of the tumor and which is produced naturally by cells of the tumor, wherein the enzyme is only produced by tumor cells or is produced at concentrations that are higher than that in normal tissues, whereby cleavage of the prosthetic group from the prodrug yields the substantially water-insoluble drug entrapped in the extracellular space, wherein the prodrug has the structure

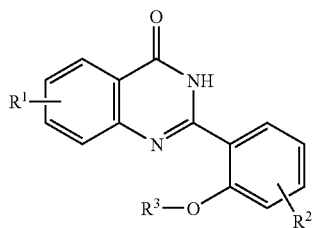

wherein
R$^1$ is selected from the group consisting of a hydrogen radical, a radionuclide, a molecule labeled with one or more radionuclides, a boron atom, a molecule labeled with one or more boron atoms, and a boron cage;
R$^2$ is selected from the group consisting of a hydrogen radical, a radionuclide, and a boron cage;
at least one of R$^1$ and R$^2$ is not a hydrogen radical; and
R$^3$ is a prosthetic group that can be cleaved from the prodrug by the enzyme.

2. The method of claim 1, wherein R$^1$ is a hydrogen radical and R$^2$ is a radionuclide.

3. The method of claim 1, wherein R$^1$ is a radionuclide and R$^2$ is a hydrogen radical.

4. The method of claim 1, wherein R$^3$ is a phosphate moiety.

5. The method of claim 1, wherein R$^3$ is a sulfate moiety.

6. The method of claim 1, wherein R$^3$ is a peptide moiety.

7. The method of claim 1, wherein R$^3$ is a sugar moiety.

8. The method of claim 1, wherein the enzyme is present in the extracellular space of the tumor at concentrations higher than in the extracellular space of normal tissues.

9. The method of claim 1, wherein the enzyme is selected from the group consisting of an acetylglucosaminidase, an acetylneuraminidase, an aldolase, an amidotransferase, an arabinopyranosidase, a carboxykinase, a deaminase, a decarboxylase, a dehydratase, a dehydrogenase, a DNAse, an endonuclease, an epimerase, an esterase, an exonuclease, a fucosidase, a galactosidase, a glucokinase, a glucosidase, a glutaminase, a glutathionase, a glucoronidase, a guanidinobenzoatase, a hexokinase, an iduronidase, a kinase, a lactase, a mannosidase, a nitrophenylphosphatase, a peptidase, a peroxidase, a phosphatase, a phosphotransferase, a protease, an RNAse, a reductase, a sulfatase, a telomerase, a transaminase, a transcarbamylase, a transferase, a xylosidase, a uricase, and a urokinase.

10. The method of claim 1, wherein the prodrug is either injected by a route selected from the group consisting of intravenously, infra-arterially, subcutaneously, into the lymphatic circulation, intraperitoneally, intrathecally, intratumorally, and intravesically, or is given orally.

11. The method of claim 1, wherein the drug comprises a radionuclide.

12. The method of claim 11, wherein the radionuclide is selected from the group consisting of a gamma emitting radionuclide, a positron emitting radionuclide, an alpha particle emitting radionuclide, and a beta particle emitting radionuclide.

13. The method of claim 12, wherein the radionuclide is an alpha particle emitting radionuclide selected from the group consisting of astatine-211, bismuth-212, and bismuth-213.

14. The method of claim 13, wherein the beta particle emitting radionuclide emits beta particles whose energies are greater than 1 keV.

15. The method of claim 12, wherein the beta particle emitting radionuclide is iodine-131, copper-67, samarium-153, gold-198, palladium-109, rhenium-186, rhenium-188, dysprosium-165, strontium-89, phosphorous-32, phosphorous-33, or yttrium-90.

16. The method of claim 1, wherein the drug comprises a boron cage.

17. The method of claim 1, wherein the prosthetic group is a phosphate group.

18. The method of claim 1, wherein the prosthetic group is a sulfate group.

19. The method of claim 1, wherein the prosthetic group is a glycoside.

20. The method of claim 1, wherein the prosthetic group is a monosaccharide.

21. The method of claim 1, wherein the prosthetic group is a polysaccharide.

22. The method of claim 1, wherein the prosthetic group is an aromatic moiety.

23. The method of claim 1, wherein the prosthetic group is an amino acid moiety.

24. The method of claim 1, wherein the prosthetic group is a polypeptide.

25. A method of in-vivo localizing a water-insoluble drug within the extracellular space of solid tumor tissue in an animal, the method comprising administering a water-soluble prodrug to the animal, wherein the prodrug comprises the drug substituted with a prosthetic group that is cleavable by an enzyme, which is present in the extracellular space of the tumor and which is produced naturally by cells of the tumor, wherein the enzyme is only produced by tumor cells or is produced at concentrations that are higher than that in normal tissues, whereby cleavage of the prosthetic group from the prodrug yields the substantially water-insoluble drug entrapped in the extracellular space, wherein the prodrug has the structure

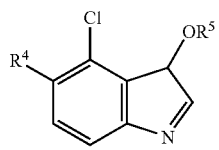

wherein
  $R^4$ is selected from the group consisting of a radionuclide, a molecule labeled with one or more radionuclides, a boron atom, a molecule labeled with one or more boron atoms, and a boron cage, and
  $R^5$ is a prosthetic group that can be cleaved from the prodrug by the enzyme.

26. The method of claim 25, wherein $R^4$ is a radionuclide $R^5$ is a beta-D-galactosidase moiety.

27. The method of claim 25, wherein the enzyme is present in the extracellular space of the tumor at concentrations higher than in the extracellular space of normal tissues.

28. The method of claim 25, wherein the enzyme is selected from the group consisting of an acetylglucosaminidase, an acetylneuraminidase, an aldolase, an amidotransferase, an arabinopyranosidase, a carboxykinase, a deaminase, a decarboxylase, a dehydratase, a dehydrogenase, a DNAse, an endonuclease, an epimerase, an esterase, an exonuclease, a fucosidase, a galactosidase, a glucokinase, a glucosidase, a glutaminase, a glutathionase, a glucoronidase, a guanidinobenzoatase, a hexokinase, an iduronidase, a kinase, a lactase, a mannosidase, a nitrophenylphosphatase, a peptidase, a peroxidase, a phosphatase, a phosphotransferase, a protease, an RNAse, a reductase, a sulfatase, a telomerase, a transaminase, a transcarbamylase, a transferase, a xylosidase, a uricase, and a urokinase.

29. The method of claim 25, wherein the prodrug is either injected by a route selected from the group consisting of intravenously, intra-arterially, subcutaneously, into the lymphatic circulation, intraperitoneally, intrathecally, intratumorally, and intravesically, or is given orally.

30. The method of claim 25, wherein the drug comprises a radionuclide.

31. The method of claim 30, wherein the radionuclide is selected from the group consisting of a gamma emitting radionuclide, a positron emitting radionuclide, an alpha particle emitting radionuclide, and a beta particle emitting radionuclide.

32. The method of claim 31, wherein the radionuclide is an alpha particle emitting radionuclide selected from the group consisting of astatine-211, bismuth-212, and bismuth-213.

33. The method of claim 32, wherein the beta particle emitting radionuclide emits beta particles whose energies are greater than 1 keV.

34. The method of claim 31, wherein the beta particle emitting radionuclide is iodine-131, copper-67, samarium-153, gold-198, palladium-109, rhenium-186, rhenium-188, dysprosium-165, strontium-89, phosphorous-32, phosphorous-33, or yttrium-90.

35. The method of claim 25, wherein the drug comprises a boron cage.

36. The method of claim 25, wherein the prosthetic group is a phosphate group.

37. The method of claim 25, wherein the prosthetic group is a sulfate group.

38. The method of claim 25, wherein the prosthetic group is a glycoside.

39. The method of claim 25, wherein the prosthetic group is a monosaccharide.

40. The method of claim 25, wherein the prosthetic group is a polysaccharide.

41. The method of claim 25, wherein the prosthetic group is an aromatic moiety.

42. The method of claim 25, wherein the prosthetic group is an aminoacid moiety.

43. The method of claim 25, wherein the prosthetic group is a polypeptide.

* * * * *